(12) United States Patent
Cherbis et al.

(10) Patent No.: US 8,565,508 B2
(45) Date of Patent: Oct. 22, 2013

(54) SYSTEM AND A METHOD FOR INSEPCTING AN OBJECT USING A HYBRID SENSOR

(75) Inventors: Yosi Cherbis, Haifa (IL); Yacov Malinovich, Kiryat Tivon (IL); Gilad Golan, Raanana (IL)

(73) Assignee: Camtek Ltd., Migdal Haemek (IL)

( * ) Notice: Subject to any disclaimer, the term of this patent is extended or adjusted under 35 U.S.C. 154(b) by 5 days.

(21) Appl. No.: 13/371,437

(22) Filed: Feb. 12, 2012
(Under 37 CFR 1.47)

(65) Prior Publication Data
US 2013/0044208 A1    Feb. 21, 2013

Related U.S. Application Data

(63) Continuation-in-part of application No. 12/626,636, filed on Nov. 26, 2009, now Pat. No. 8,358,829.

(51) Int. Cl.
*G06K 9/00* (2006.01)

(52) U.S. Cl.
USPC ............... 382/141; 348/125; 356/237.4

(58) Field of Classification Search
USPC .............. 382/138–154; 348/125, E07.085; 356/237.1–237.5
See application file for complete search history.

(56) References Cited

U.S. PATENT DOCUMENTS

| | | | | |
|---|---|---|---|---|
| 5,358,829 A * | 10/1994 | Tang et al. | ..................... | 430/386 |
| 8,213,704 B2 * | 7/2012 | Peterson et al. | .............. | 382/145 |
| 2003/0043286 A1 * | 3/2003 | Kato | ............................. | 348/246 |
| 2012/0189189 A1 * | 7/2012 | Doe et al. | ...................... | 382/149 |

* cited by examiner

*Primary Examiner* — Hoa Pham
(74) *Attorney, Agent, or Firm* — Oren Reches

(57) ABSTRACT

A method and an inspection system may be provided. The inspection system may include (a) a hybrid sensor that may include a monochromatic portion that is arranged to obtain a monochromatic image of a first area of an object; a multiple-color portion that is arranged to obtain a multi-colored image of a second area of the object; wherein the monochromatic portion comprises monochromatic sensing elements that sense radiation of a same frequency band; wherein the multiple-color portion comprises color sensing elements of different types, wherein different types of color sensing elements are associated with different frequency bands; (b) a storage element arranged to store the monochromatic image and the multiple-color image; and (c) a defect detection module arranged to detect defects by processing at least one of the monochromatic image and the multiple-color image.

19 Claims, 8 Drawing Sheets

610 receiving from an external camera first image information and second image information, wherein the first image information pertains to a first image that is an image comprising color information of a first band of an optical spectrum and the second image information pertains to a second image that is an image comprising color information of a second band of the optical spectrum, wherein the first image and the second image cover substantially the same area

620 processing the first image information so as to detect first type defects and processing the second image information so as to detect second type defects

630 generating a defect alert and/or a defect report, in response to results of the processing of the different images

| 132 | 142 | 132 | 142 | 132 | 142 | 132 | 142 |
|-----|-----|-----|-----|-----|-----|-----|-----|
| 142 | 132 | 142 | 132 | 142 | 132 | 142 | 132 |
| 132 | 142 | 132 | 142 | 132 | 142 | 132 | 142 |
| 142 | 132 | 142 | 132 | 142 | 132 | 142 | 132 |
| 132 | 142 | 132 | 142 | 132 | 142 | 132 | 142 |
| 142 | 132 | 142 | 132 | 142 | 132 | 142 | 132 |
| 132 | 142 | 132 | 142 | 132 | 142 | 132 | 142 |
| 142 | 132 | 142 | 132 | 142 | 132 | 142 | 132 |

1300

| 132 | 132 | 132 | 132 | 132 | 132 | 132 | 132 |
|-----|-----|-----|-----|-----|-----|-----|-----|
| 142 | 142 | 142 | 142 | 142 | 142 | 142 | 142 |
| 132 | 132 | 132 | 132 | 132 | 132 | 132 | 132 |
| 142 | 142 | 142 | 142 | 142 | 142 | 142 | 142 |
| 132 | 132 | 132 | 132 | 132 | 132 | 132 | 132 |
| 142 | 142 | 142 | 142 | 142 | 142 | 142 | 142 |
| 132 | 132 | 132 | 132 | 132 | 132 | 132 | 132 |
| 142 | 142 | 142 | 142 | 142 | 142 | 142 | 142 |

SYSTEM AND A METHOD FOR INSEPCTING AN OBJECT USING A HYBRID SENSOR

RELATED APPLICATIONS

This patent application is a continuation in part of U.S. patent application Ser. No. 12/626,636 filing date Nov. 26, 2009 and claims the priority of U.S. Provisional Patent application Ser. No. 61/442,247, filing date Feb. 13, 2011, which is incorporated herein by its entirety.

BACKGROUND OF THE INVENTION

Various articles are inspected by inspection systems such as automatic optical inspection (AOI) systems. The AOI systems are required to be fast and accurate.

There may be a trade off between the throughput of the AOI system and the manner in which the AOI system images articles. For example, multi-color sensors can provide more detailed information than monochromatic sensors but the processing of multi-color information and the retrieval of such multi-color information can consume more time and be more complex than the retrieval and/or processing of monochromatic information.

SUMMARY

According to an embodiment of the invention an inspection system may be provided and may include a hybrid sensor that may include a monochromatic portion that is arranged to obtain a monochromatic image of a first area of an object; a multiple-color portion that is arranged to obtain a multi-colored image of a second area of the object; wherein the monochromatic portion may include monochromatic sensing elements that sense radiation of a same frequency band; wherein the multiple-color portion may include color sensing elements of different types, wherein different types of color sensing elements are associated with different frequency bands; a storage element arranged to store the monochromatic image and the multiple-color image; and a defect detection module arranged to detect defects by processing at least one of the monochromatic image and the multiple-color image.

The defect detection module may be arranged to process the monochromatic image to provide intermediate defect detection results; determine whether to process the multiple-color image based upon the intermediate defect detection results; and process at least a portion of the multiple-color image to detect defects if it is determined to process the multiple-color image.

The defect detection module may be arranged to process the monochromatic image to provide intermediate defect detection results; determine to process the multiple-color image if the intermediate defect detection results are indicative of suspected defects; and process at least a portion of the multiple-color image to detect defects if it is determined to process the multiple-color image.

The inspection system wherein the defect detection module may be arranged to: process the monochromatic image to provide intermediate defect detection results; determine to process the multiple-color image if the intermediate defect detection results are indicative of suspected defects of at least a predefined amount of probability; and process at least a portion of the multiple-color image to detect defects if it is determined to process the multiple-color image.

The hybrid sensor may be arranged to provide the monochromatic image at a resolution that is higher than a resolution of the multiple-color image.

The frequency band of the monochromatic sensing elements may comprise all the frequency bands of the color sensing elements.

The frequency band of the monochromatic sensing elements may be a broadband frequency band and wherein the frequency bands of the color sensing elements may be narrowband frequency bands.

The frequency band of the monochromatic sensing elements may all the frequency bands of the color sensing elements.

The monochromatic portion may include multiple adjacent rows of monochromatic sensing elements; and wherein the multiple-color portion may include multiple columns, each column may include color sensing elements that are arranged to sense the same frequency band.

The monochromatic portion may include multiple adjacent rows of monochromatic sensing elements; and wherein the multiple-color portion may include multiple columns, each column may include color sensing elements of different frequency bands.

The monochromatic portion may include multiple adjacent rows of monochromatic sensing elements; and wherein the multiple-color portion may include color sensing elements of different frequency bands that are arranged in an interleaved manner.

The hybrid sensor may include multiple repetitions of a combination that may include a set of monochromatic sensing elements and color sensing elements of different frequency bands.

The hybrid sensor may include multiple repetitions of a combination that may include a row of monochromatic sensing elements and at least one row of color sensing elements of different frequency bands.

The first area may equal the second area. The first and second areas may differ from each other.

At least one frequency band may include infra red radiation and at least one frequency band may include visible light radiation.

At least one frequency band may include infra red radiation and at least one frequency band may include ultra violet radiation.

The monochromatic sensing elements may be grouped in a group that has a shape that differs from a line.

A defect detection method may be provided according to an embodiment of the invention and may include obtaining a hybrid image by a hybrid sensor, the hybrid sensor may include (a) a monochromatic portion that may be arranged to obtain monochromatic image of a first area of an object; (b) a multiple-color portion that may be arranged to obtain a multi-colored image of a second area of the object; wherein the monochromatic portion may include monochromatic sensing elements that sense radiation of a same frequency band; wherein the multiple-color portion may include color sensing elements of different types, wherein different types of color sensing elements are associated with different frequency bands; wherein the hybrid image may include the monochromatic image and the multi-colored image; and applying a defect detection process on at least one of the monochromatic image and the multiple-color image and on at least zero reference images.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

FIG. 4 illustrates a system for inspecting an object, according to an embodiment of the invention;

FIG. 5 illustrates various arrangements of sensors according to various embodiments of the invention;

DETAILED DESCRIPTION OF THE DRAWINGS

Figure 1:
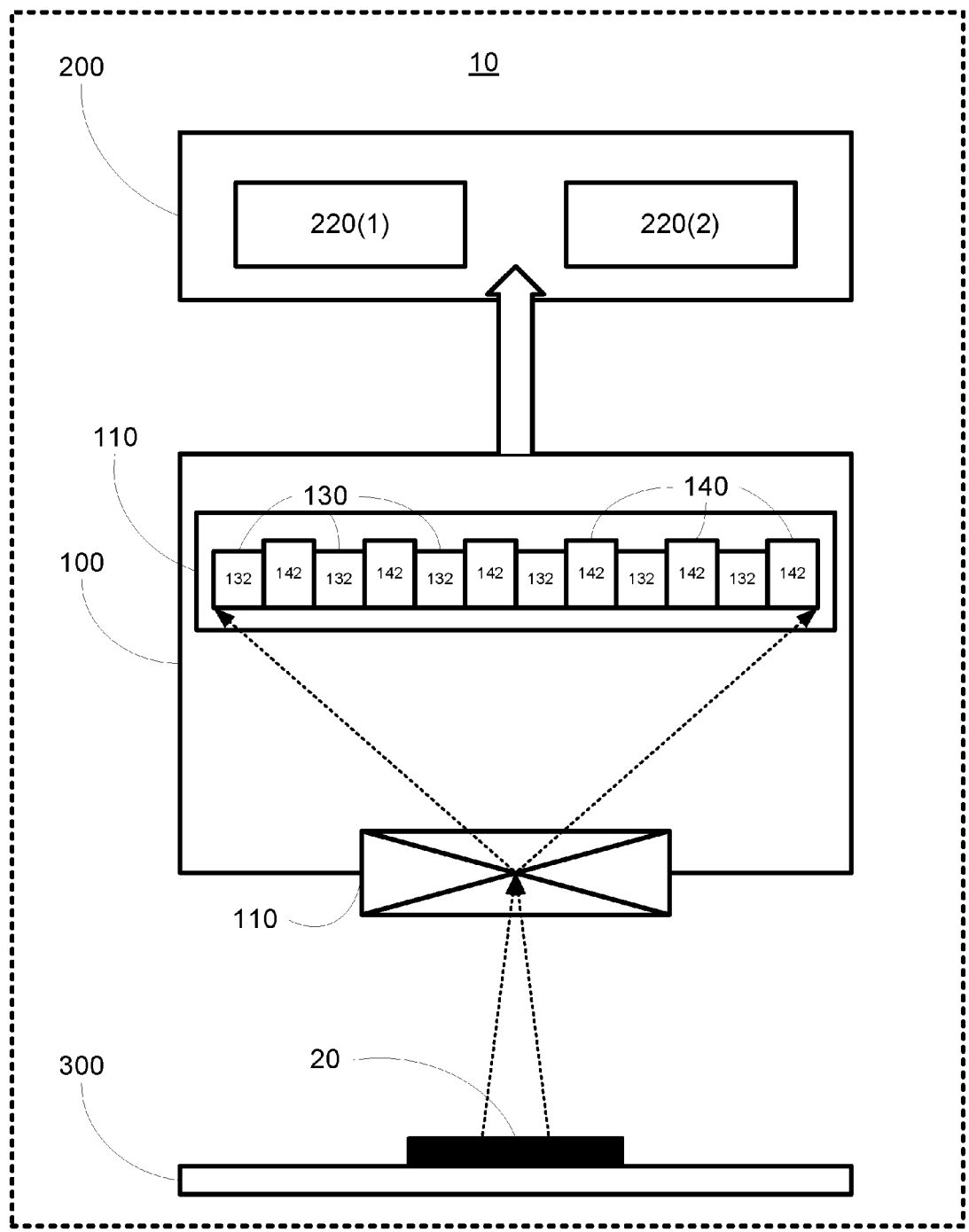
FIG. 1 illustrates a system for inspecting an object, according to an embodiment of the invention.

The foregoing and other objects, features, and advantages of the present invention will become more apparent from the following detailed description when taken in conjunction with the accompanying drawings. In the drawings, similar reference characters denote similar elements throughout the different views.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

In the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

FIG. 1 illustrates system 10 for inspecting an object, according to an embodiment of the invention.

System 10 includes camera 100 that includes optical section 110 for projecting an image of an object such as inspected electronic circuit 20 (that can be a Printed Circuit Board) onto electronic detector 120, wherein electronic detector 120 includes at least a first group of sensors 130 (that includes at least one first type pixel sensors 132 for the capturing of light signals of a first band of an optical spectrum), and a second group of sensors 140 (that includes at least one second type pixel sensors 142 for the capturing of light signals of a second band of the optical spectrum). It is noted that the pixels sensors of both the first and second groups of sensors 130 and 140 are conveniently adapted to acquire light signals substantially parallelly (i.e. at least partly concurrently). The pixel sensors can be elements of a sensor array.

The object can be imaged, one area after the other, by a multiple iteration process. During each of these iterations an area of the inspected image is illuminated and an image of that area is projected to the first and second groups of sensors.

Each of the first and second groups of sensors can receive the same image but this is not necessarily so. For example, adjacent sensors can receive adjacent portions of the same image. The former can occur when each area is illuminated once while the latter can occur when the same area pixels are illuminated (and light is sensed) more than once. If, for example, the area is scanned then the sensors of the different groups will eventually receive light from the entire area.

Each sensor is arranged to sense light components and to generate detection signals that represents the sensed light components. The detection signals can be analog signals, digital signals, gray level signals, and the like. The detection signals can be stored in memory units and fed to a processing unit.

It is noted that the optical spectrum may be limited to the visible optical spectrum, or may extend to other parts of the optical spectrum, such as infra red.

The first and the second band may be referred to as a color (e.g. red light, green light), but this is not necessarily so. Further more, each of the types of pixel sensors may be adapted to detect light substantially from the respective band of the optical spectrum, or alternatively, the light arriving from the optical section (optics) 110 may be filtered before arriving to different pixel sensors (e.g. red filters will filter light that is directed to red band pixel sensors, and so forth).

System 10 further include a processing unit 200 for processing first image information that is received from camera 100, and second image information that is received from camera 100, wherein first image information pertains to image information of a first image which is respective to light signals detected by first type pixel sensors 132, and second image information pertains to image information of a second image which is respective to light signals detected by second type pixel sensors 142, wherein the first image and the second images are images of substantially the same area.

The processing unit 200 can correlate between the detection signals received from both groups of sensors and detect defects. At least some defects may be detected only if they appear in detection signals from both groups of sensors.

It is noted that processing unit 200 may be connected to camera 100 according to different embodiments of the invention either wirelessly or via cables, and that the connection may involve one or more intermediate units (which may and may not manipulate the transferred image information).

Processing unit 200 is configured to process first image information so as to detect first type defects, and to process second image information so as to detect second type defects, wherein it is noted that, according to different embodiments of the invention, each type of image information may be used to detect more than a single type of defect. For example, in printed circuit boards (PCB), a red image information may be processed to detect defects in metal components (e.g. copper, gold), and a green or white image information may be processed to detect defects in a solder mask, and to evaluate coverage. It is noted that system 10 may be used for detecting defects in different types of electronic circuits 20, such as PCBs, integrated circuits, and so forth. It is noted that processing unit 200 may include one or more processors 220(1) and 220(2) for the processing of image information.

It is noted that system 10 may be used as an automatic final inspection, carrying out a last stage in a process of inspection. System 10 may be used as an automated optical inspection system.

According to an embodiment of the invention, system 10 (and especially processing unit 200) may be configured to generate a defect alert and/or a defect report, in response to results of the processing of the different images.

It is noted that electronic detector 120 may further include at least one additional group of sensors that includes at least one pixel sensor for the capturing of light signals of another band of an optical spectrum. For example, a third group of sensors may include pixel sensors for the capturing of a green portion of the spectrum.

It is noted that, according to an embodiment of the invention, camera 100 is an RGB camera. According to an embodiment of the invention, camera 100 is a CMOS (Complementary Metal Oxide Semiconductor) camera. According to an embodiment of the invention, camera 100 is a three line CCD (Charge-coupled device) camera.

According to an embodiment of the invention, processing unit 200 includes one or more processors 220 that are adapted to parallelly process image information of the first image and of the second image.

According to an embodiment of the invention, system 10 further includes inspection surface 300 that is adapted to support the electronic circuit 20 during the scanning process. According to an embodiment of the invention, system 10 is adapted to transfer the scanned electronic circuit 20 to another machine or location, in response to a result of the processing.

Figure 2:
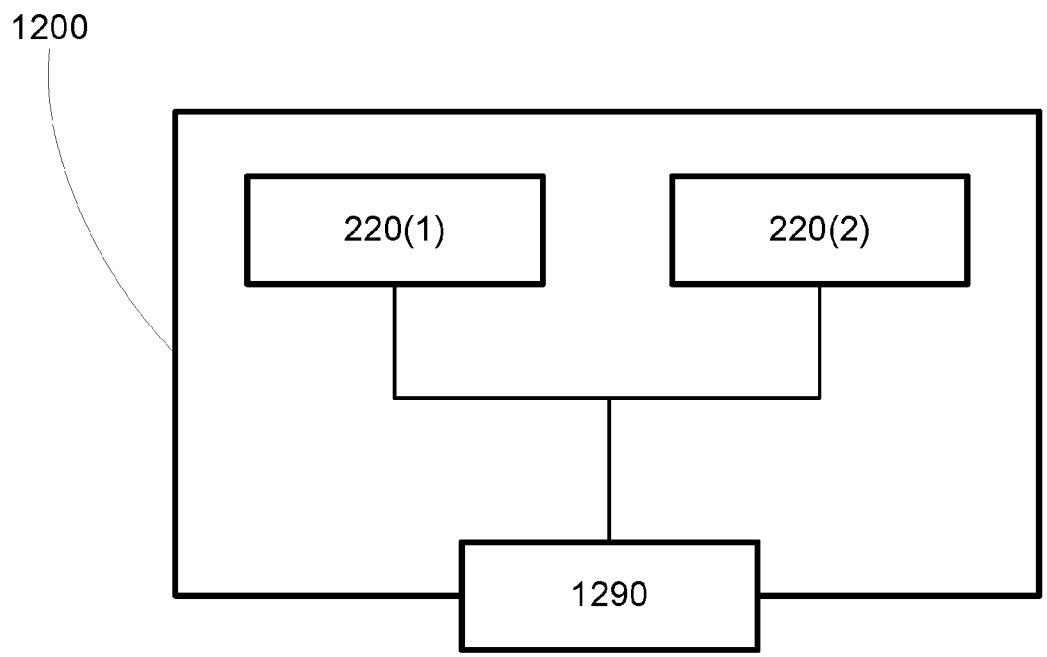
FIG. 2 illustrates a system for inspecting an object, according to an embodiment of the invention.

FIG. 2 illustrates system 1200 for inspecting an object, according to an embodiment of the invention.

System 1200 includes interface 1290 for receiving from an external camera image information that includes first image information that pertains to a first image that is an image comprising color information of a first band of an optical spectrum (e.g. red color information) and second image information that pertains to a second image that is an image comprising color information of a second band of the optical spectrum (e.g. green color information), wherein the first image and the second image cover substantially the same area.

According to an embodiment of the invention, the first image information and the second image information are both part of an image information of a single image, and pertains to different colors of which (e.g. in a RGB camera). It is noted that the first image information and the second image information are acquired substantially parallelly (i.e. at least partly concurrently).

System 1200 further includes one or more processors 1220 configured to process first image information so as to detect first type defects, and to process second image information so as to detect second type defects, wherein it is noted that, according to different embodiments of the invention, each type of image information may be used to detect more than a single type of defect.

It is noted that system 1200 may be used in an automatic final inspection system, carrying out a last stage in a process of inspection. System 1200 may be used in an automated optical inspection system.

According to an embodiment of the invention, system 1200 (and especially the one or more processors 1220) may be configured to generate a defect alert and/or a defect report, in response to results of the processing of the different images.

According to an embodiment of the invention, the one or more processors 1220 are adapted to parallelly process image information of the first image and of the second image. It is noted that, according to an embodiment of the invention, the one or more processors 1220 are adapted to process image information that is received from the external camera, to provide the first and the second image information (e.g. if the external camera provides image information of a color image including both the first and the second bands of the optical spectrum).

Figure 3:
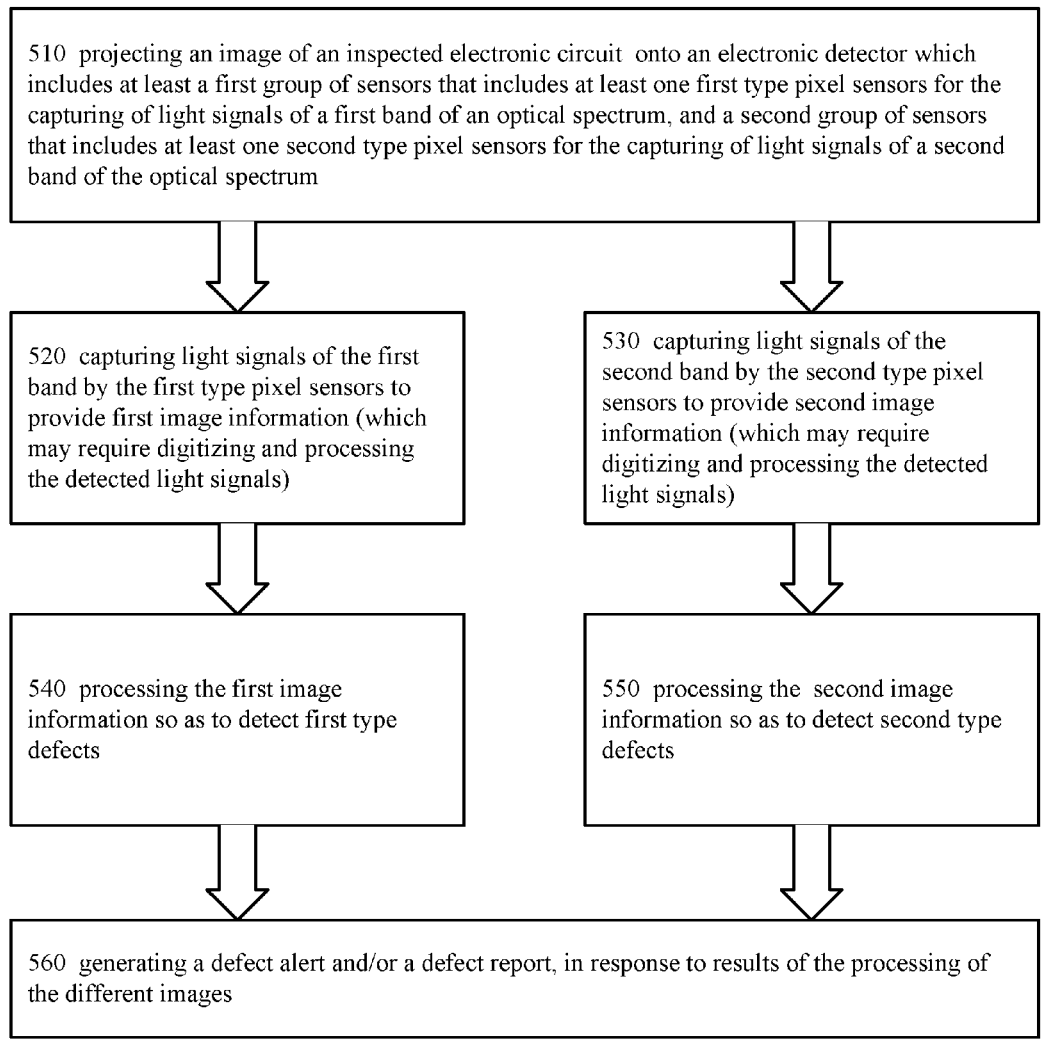
FIG. 3 illustrates a method for inspecting an object, according to an embodiment of the invention.

FIG. 3 illustrates method 500 for electronic circuit scanning, according to an embodiment of the invention.

Method 500 conveniently starts with stage 510 of projecting an image of an inspected electronic circuit (such as a PCB, or an IE) onto an electronic detector which includes at least a first group of sensors that includes at least one first type pixel sensors for the capturing of light signals of a first band of an optical spectrum, and a second group of sensors that includes at least one second type pixel sensors for the capturing of light signals of a second band of the optical spectrum.

Stage 510 is followed by stage 520 of capturing light signals of the first band by the first type pixel sensors to provide first image information (which may require digitizing and processing the detected light signals), and stage 530 of capturing light signals of the second band by the second type pixel sensors to provide second image information (which may require digitizing and processing the detected light signals), wherein stage 520 and 530 are conveniently carried out substantially parallelly (i.e. at least partly concurrently), wherein the first image information pertains to image information of a first image which is respective to light signals detected by first type pixel sensors, and the second image information pertains to image information of a second image which is respective to light signals detected by second type pixel sensors, wherein the first image and the second images are images of substantially the same area.

It is noted that the optical spectrum may be limited to the visible optical spectrum, or may extend to other parts of the optical spectrum, such as infra red. The first and the second band may be referred to as a color (e.g. red light, green light), but this is not necessarily so. Further more, each of the types of pixel sensors may be adapted to detect light substantially from the respective band of the optical spectrum, or alternatively, the light arriving from the optical section may be filtered before arriving to different pixel sensors (e.g. red filters will filter light that is directed to red band pixel sensors, and so forth).

Stages 520 and 530 are followed by stage 540 of processing the first image information so as to detect first type defects, and by stage 550 of processing the second image information so as to detect second type defects, wherein stages 540 and 550 may be carried out substantially in parallel, serially, or in other temporal relation, according to different embodiments of the invention. It is noted that, according to different embodiments of the invention, each type of image information may be used to detect more than a single type of defect. For example, in printed circuit boards (PCB), a red image information may be processed to detect defects in metal components (e.g. copper, gold), and a green or white image information may be processed to detect defects in a solder mask, and to evaluate coverage. It is noted that method 500 may be used for detecting defects in different types of electronic circuits, such as PCBs, integrated circuits, and so forth.

According to an embodiment of the invention, method 500 further includes stage 560 of generating a defect alert and/or a defect report, in response to results of the processing of the different images.

Referring to the examples set forward in the previous figures, method 500 may be carried out by system 10.

FIG. 4 illustrates method 600 for electronic circuit scanning, according to an embodiment of the invention.

Method 600 conveniently starts with stage 610 receiving from an external camera first image information and second image information, wherein the first image information pertains to a first image that is an image comprising color information of a first band of an optical spectrum (e.g. red color information) and the second image information pertains to a second image that is an image comprising color information of a second band of the optical spectrum (e.g. green color information), wherein the first image and the second image cover substantially the same area. It is noted that conveniently the first image and the second image are obtained by the external camera substantially in parallel.

Stage 610 is followed by stage 620 of processing the first image information so as to detect first type defects and processing the second image information so as to detect second type defects, wherein the processing of the first image information and the processing of the second image information may be carried out substantially in parallel, serially, or in other temporal relation, according to different embodiments of the invention. It is noted that, according to different embodiments of the invention, each type of image information may be used to detect more than a single type of defect. For example, in printed circuit boards (PCB), a red image information may be processed to detect defects in metal components (e.g. copper, gold), and a green or white image information may be processed to detect defects in a solder mask, and to evaluate coverage. It is noted that method 600 may be used for detecting defects in different types of electronic circuits, such as PCBs, integrated circuits, and so forth.

According to an embodiment of the invention, method 600 further includes stage 630 of generating a defect alert and/or a defect report, in response to results of the processing of the different images.

Referring to the examples set forward in the previous figures, method 600 may be carried out by system 1200.

FIG. 5 illustrates various arrangements of sensors according to various embodiments of the invention.

Array 1300 includes first type pixel sensors 132 and second type pixel sensors 142 that are arranged in an interlaced manner to form a two dimensional sensor array. Each row of the array includes both pixel sensors of a first type 132 and pixel sensors of a second type 142. Each first type pixel 132 is surrounded by four second type pixel sensors 142. Each second type pixel 142 is surrounded by four first type pixel sensors 132.

A pixel sensor is a sensor that its detection signals may affect a pixel of an image that may be reconstructed by the processing unit.

Array 1400 includes dedicated rows of first type pixel sensors 132 and dedicated rows of second type pixel sensors 142. Each row of first type pixel sensors 132 is surrounded by two rows of second type pixel sensors 142.

The terms cells and sensing elements are used interchangeably in the following text.

According to an embodiment of the invention a hybrid sensor is provided and a system that includes a hybrid sensor is provided. According to an embodiment of the invention the hybrid sensor can include monochromatic cells and multiple-color cells. The hybrid sensor can include, for example, about 1000 sensing element per row (or column) and can include a matrix of about 1,000,000 sensing elements. It is noted that other amounts of sensing elements per hybrid sensor can be provided.

According to an embodiment of the invention an inspection system may be provided and may include:

a. A hybrid sensor that includes (a) a monochromatic portion (for example—gray scale black and white) that may be arranged to obtain a monochromatic image of a first area of an object; (b) a multiple-color portion that may be arranged to obtain a multi-colored image of a second area of the object; wherein the monochromatic portion comprises monochromatic sensing elements that sense radiation of a same (for example—wideband) frequency band; wherein the multiple-color portion comprises color sensing elements of different types, wherein different types of color sensing elements are associated with different frequency bands;

b. A storage element arranged to store the monochromatic image and the multiple-color image; and c. A defect detection module arranged to apply a defect detection process on at least one of the monochromatic image and the multiple-color image and on at least zero reference images. The defect detection module can be implemented by a processor. The defect detection process may include any known defect detection process such as but not limited to object to reference object comparison, object to golden reference comparison. The object can be a wafer and thus die-to-die, cell-to-cell or die to golden die comparisons can be provided.

The detection module may be arranged to:

a. Process the monochromatic image to provide intermediate defect detection results;

b. Determine whether to process the multiple-color image based upon the intermediate defect detection results; and c. Process the multiple-color image to detect defects if it is determined to process the multiple-color image.

The defect detection module may be arranged to:

a. Process the monochromatic image to provide intermediate defect detection results;

b. Determine to process the multiple-color image if the intermediate defect detection results are indicative of suspected defects; and c. Process the multiple-color image to detect defects if it is determined to process the multiple-color image.

The term "color" in the phrase "multiple-color" may include visible light frequency bands, infra-red frequency bands, ultra-violet frequency band, or a combination thereof.

The defect detection module may be arranged to:

a. Process the monochromatic image to provide intermediate defect detection results;

b. Determine to process the multiple-color image if the intermediate defect detection results are indicative of suspected defects of at least a predefined amount of probability; and c. Process the multiple-color image to detect defects if it is determined to process the multiple-color image.

The hybrid sensor may be arranged to provide the monochromatic image at a resolution that is higher than a resolution of the multiple-color image. This can be attributed to the higher density of monochromatic sensing elements in relation to the density of color sensing elements of the same type at the multiple-color portion of the hybrid sensor.

The frequency band of the monochromatic sensing elements may include all of the frequency bands of the color sensing elements and/or the Near Infra Red (NIR) band.

The frequency band of the monochromatic sensing elements may be a broadband frequency band and the frequency bands of the color sensing elements may be narrowband frequency bands.

A broadband frequency sensing element can be a sensing element that senses radiation without any spectral filtering. This sensing element may exhibit the natural response of the sensor.

A narrowband frequency sensing element can be a sensing element that senses a part of the radiation—after spectral filtering.

The frequency band of the monochromatic sensing elements may include a combination of some (but not all) of the frequency bands of the color sensing elements. The frequency band of the monochromatic sensing elements may be a narrow frequency band. At least one color sensing element can have a wideband frequency band.

At least one color sensing element can have a frequency band that is wider than the frequency band of the monochromatic sensing element.

The monochromatic portion may include multiple adjacent rows of monochromatic sensing elements; and the multiple-color portion may include multiple columns, each column may include color sensing elements that are arranged to sense a same frequency band. An example is provided in table 4.

The monochromatic portion may include multiple adjacent rows of monochromatic sensing elements; and wherein the multiple-color portion may include multiple columns, each column may include color sensing elements of different frequency bands.

The monochromatic portion may include multiple adjacent rows of monochromatic sensing elements; and wherein the multiple-color portion may include color sensing elements of different frequency bands that are arranged in an interleaved manner. Examples are provided in tables 1 and 3.

The hybrid sensor may include multiple repetitions of a combination that may include a set of monochromatic sensing elements and color sensing elements of different frequency bands. An example is provided in FIGS. 1 and 2.

The hybrid sensor may include multiple repetitions of a combination that may include a row of monochromatic sensing elements and at least one row of color sensing elements of different frequency bands. An example is provided in table 1.

The first area (imaged by the monochromatic sensing elements) may equal the second area or may differ from the second area (imaged by the multiple-color sensing elements). The first and second areas can partially overlap.

At least one sensing element can sense infra red radiation and at least one sensing element may sense visible light radiation.

At least one sensing element can sense infra red radiation and at least one sensing element may sense ultra violet radiation.

At least one sensing element can sense ultra violet radiation and at least one sensing element may sense visible light radiation.

The monochromatic sensing elements may be grouped in a group that has a shape that differs from a line.

A hybrid sensor can include multiple groups of sensing elements (cells), wherein different groups of sensing elements are responsive to different light bands, one light band may be a wide radiation band and at least one other light band can be limited width (narrowband) radiation bands.

For example, the wide radiation band can include multiple narrowband radiation bands and may also include all the narrowband radiation bands. For example—the wide radiation band can include the visible light spectrum while the different narrowband radiation bands can include green light, red light and blue light.

The color cells of the hybrid sensor can be arranged in one or more groups of one or more shapes and the monochromatic cells can be arranged in one or more other groups of one or more shapes.

Figure 6:
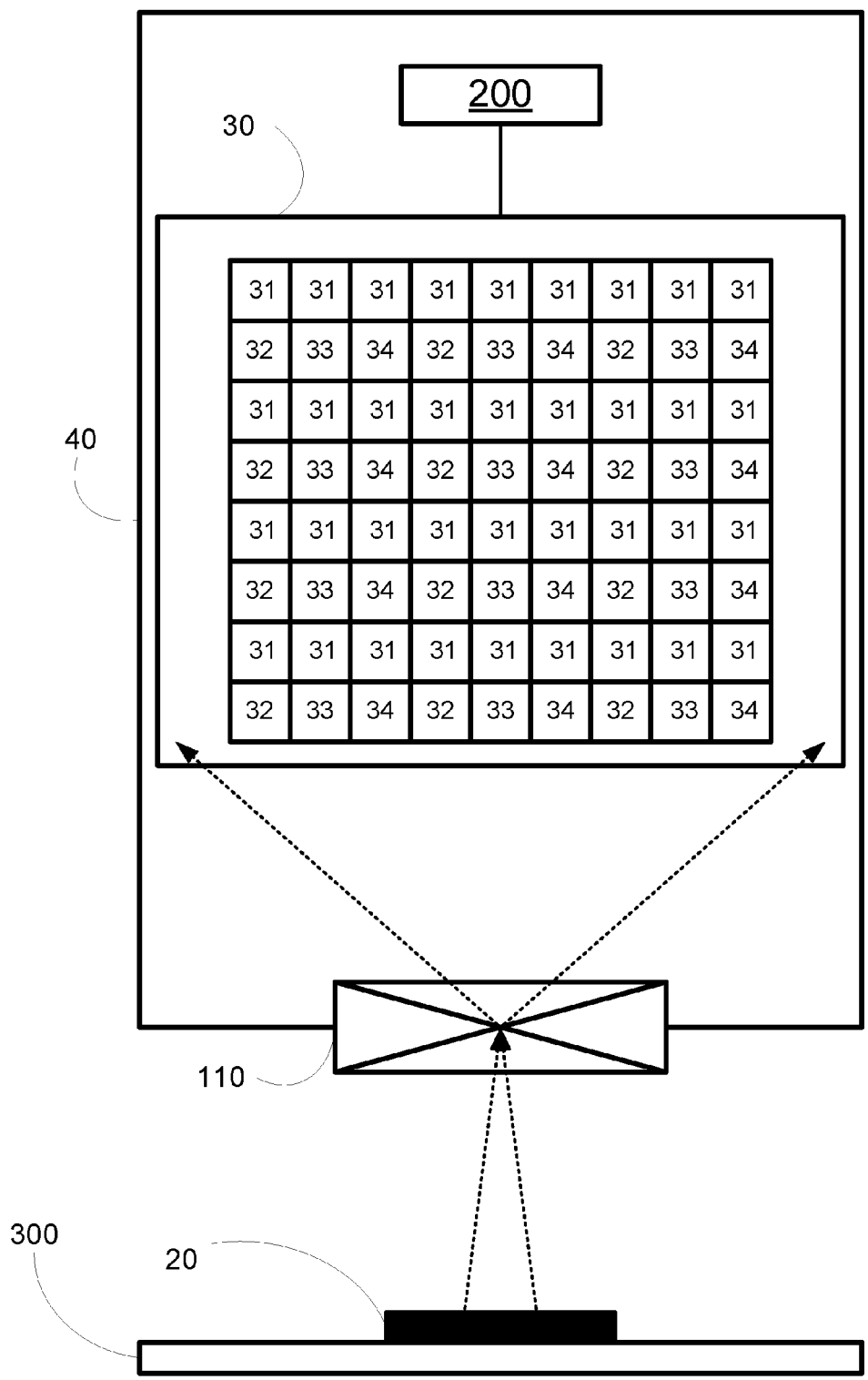
FIG. 6 illustrates a system for inspecting an object, according to an embodiment of the invention.

FIG. 6 illustrates a system 60 that includes camera 40 that includes optical section 110 for projecting an image of an object such as inspected electronic circuit 20 (that can be a Printed Circuit Board) onto electronic detector 120, wherein electronic detector 120 includes a hybrid sensor 30.

Hybrid sensor 30 may include cells of different types—one type of cells for obtaining monochromatic (for example wideband) information and multiple types for obtaining narrowband information (such as red, green and blue respectively).

FIG. 6 and table 1 illustrate an example of one possible configuration of the hybrid sensor 30. In table 1 a gray level sensing cell is denoted GL and in FIG. 6 it is denoted 31. In table 1 a red sensing cell is denoted R and in FIG. 6 it is denoted 32. In table 1 a green sensing cell is denoted G and in FIG. 6 it is denoted 33. In table 1 a blue sensing cell is denoted B and in FIG. 6 it is denoted 34.

Table 1 illustrates an arrangement of cells of a hybrid sensor according to another embodiment of the invention:

TABLE 1

| GL | GL | GL | GL | GL | GL | GL | GL | GL |
|----|----|----|----|----|----|----|----|----|
| R  | G  | B  | R  | G  | B  | R  | G  | B  |
| GL | GL | GL | GL | GL | GL | GL | GL | GL |
| R  | G  | B  | R  | G  | B  | R  | G  | B  |
| GL | GL | GL | GL | GL | GL | GL | GL | GL |
| R  | G  | B  | R  | G  | B  | R  | G  | B  |

Table 2 illustrates a hybrid sensor that includes a monochromatic line (a line that includes cells of that are sensitive to a wide radiation band) and a multi-color line (that includes cells that are sensitive to different narrow/limited radiation bands).

The monochromatic line can include only one type of cells out of, for example, gray level cells, cells of a certain color (red, green or blue or any other color), Infra Red cells and Ultra Violet cells.

A multi-color line can include cells of three or more types of cells out of, for example, gray level cells, cells of a certain color (red, green or blue or any other color), Infra Red cells and Ultra Violet cells. Usually a type of cell which is not identical to the monochromatic cell type.

Lines or groups of different types can be proximate to each other and may have fields of view that overlap or at least partially overlap.

A hybrid sensor can include multiple lines of each type (monochromatic lines and multiple lines cells) that may be arranged in an interlaced manner.

A hybrid sensor can include monochromatic lines that differ from each other by the radiation band they sense. Thus a visible monochromatic line can be followed (or be spaced apart from) a UV monochromatic line.

A hybrid sensor can include N monochromatic lines (or groups) and M multi-color lines (or groups), wherein M can equal N but can differ from N.

It is noted that cells can be grouped in groups having shapes that differ from lines. For example, monochromatic cells can be arranged in rectangles, circles, rings and the like.

Multi-color group of cells can be arranged in various manner or patterns, such as but not limited to a Red-Green-Blue pattern.

The numbers of cells of different types per a multi-color group of cells may differ from each other or may equal to each other. A multi-color group of K cells can include k (1)-k (n) cells of n different types of cells, respectively. There can be any relationship between k (1) till k (n).

The different cells of the hybrid sensor can be connected to one or more memory circuits and/or retrieval circuits. If multiple memory and/or retrieval circuits are provided—each memory and/or retrieval circuit can be allocated to one or more types of cells.

Figure 7:
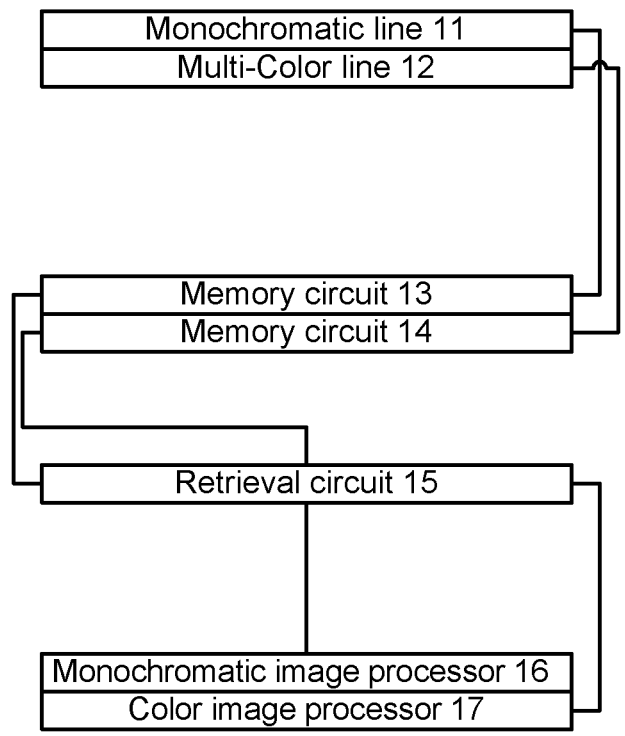
FIG. 7 illustrates a system according to an embodiment of the invention.

For example, referring to FIG. 7, a system 19 is illustrated that includes two pixel lines 11 and 12 of hybrid sensor 30 are connected to two memory circuits 13 and 14, and a retrieval circuit 15 that may output selected detection signals to one or more processing circuits such as monochromatic image processor 16 and color image processor 17.

The memory and/or retrieval cells can be arranged to ignore detection signals generated by one or more groups of cells during certain exposure periods and to store and/or output detection signals generated by one or more other group of cells during other exposure periods. Thus, for example, the hybrid sensor can output detection signals from one or more monochromatic groups of cells during a certain exposure (or retrieval) period and can output detection signals from one or more multi-color groups of cells during another exposure (or retrieval) period.

The monochromatic lines provide information that may have sharper (higher) spatial resolution than each of the different colors of a multi-color group of cells—especially when the density of the monochromatic cells is higher than the density of each color cell of the multiple-color group of cells.

An inspection system can include one or more hybrid sensors and can obtain images of an inspected object during one or more exposure sequences.

According to an embodiment of the invention an inspection system can scan an inspected article to obtain a monochromatic image and then scan the inspected article to obtain a multi-color image.

It is noted that the number of colors per each multi-color group can differ from 3 and that the numbers of color cells per multi-color groups can differ from each other or can be equal to each other.

An inspection method can utilize the hybrid sensor. For example, the inspection method can include a first phase for grabbing hybrid image of the object under inspection, a second phase of detecting suspected defects using monochrome image (or images) and a third phase of improved analysis of the suspected defects that may be used to improve the defect detection accuracy and reliability (like less false alarms) using the multi-color cells. All stages can be executed in parallel.

The following text further illustrates the arrangement of various hybrid sensors. R denotes a red cell, B denotes a blue cell, G denotes a green cell and GL denotes a white color (gray level) cell.

Table 2 illustrates an arrangement of cells of a hybrid sensor according to an embodiment of the invention:

TABLE 2

| GL | GL | GL | GL | GL | GL | GL | GL | GL |
|----|----|----|----|----|----|----|----|----|
| R  | G  | B  | R  | G  | B  | R  | G  | B  |

Multiple repetitions of the hybrid sensor of table 2 may form the hybrid sensor of table 1.

Table 3 illustrates an arrangement of cells of a hybrid sensor according to a further embodiment of the invention.

TABLE 3

| GL | GL | GL | GL | GL | GL | GL | GL | GL |
|----|----|----|----|----|----|----|----|----|
| GL | GL | GL | GL | GL | GL | GL | GL | GL |
| GL | GL | GL | GL | GL | GL | GL | GL | GL |
| GL | GL | GL | GL | GL | GL | GL | GL | GL |
| R  | G  | B  | R  | G  | B  | R  | G  | B  |
| G  | B  | R  | G  | B  | R  | G  | B  | R  |
| B  | R  | G  | B  | R  | G  | B  | R  | G  |
| R  | G  | B  | R  | G  | B  | R  | G  | B  |

Table 4 illustrates an arrangement of cells of a hybrid sensor according to yet another embodiment of the invention.

TABLE 4

| GL | GL | GL | GL | GL | GL | GL | GL | GL |
|----|----|----|----|----|----|----|----|----|
| GL | GL | GL | GL | GL | GL | GL | GL | GL |
| GL | GL | GL | GL | GL | GL | GL | GL | GL |
| GL | GL | GL | GL | GL | GL | GL | GL | GL |
| R  | G  | B  | R  | G  | B  | R  | G  | B  |
| R  | G  | B  | R  | G  | B  | R  | G  | B  |
| R  | G  | B  | R  | G  | B  | R  | G  | B  |
| R  | G  | B  | R  | G  | B  | R  | G  | B  |

Table 5 illustrates an arrangement of cells of a hybrid sensor according to yet another embodiment of the invention.

TABLE 5

| GL | GL | GL | GL | GL | GL |
|----|----|----|----|----|----|
| GL | GL | GL | GL | GL | GL |
| GL | GL | GL | GL | GL | GL |
| R  | R  | B  | B  | G  | G  |
| G  | G  | R  | R  | B  | B  |
| B  | B  | G  | G  | R  | R  |

The following tables provide additional examples of hybrid sensor configurations. The monochromatic portion includes sensing elements of the same type that have a frequency band that may be a narrowband frequency band.

IR indicates an infra red sensing element and UV indicates an ultraviolet sensing element.

TABLE 6

| R  | R | R | R  | R | R | R  | R | R |
|----|---|---|----|---|---|----|---|---|
| GL | G | B | GL | G | B | GL | G | B |
| R  | R | R | R  | R | R | R  | R | R |
| GL | G | B | GL | G | B | GL | G | B |
| R  | R | R | R  | R | R | R  | R | R |
| GL | G | B | GL | G | B | GL | G | B |

TABLE 7

| B | B | B | B | B | B | B | B | B |
|---|---|---|---|---|---|---|---|---|
| B | B | B | B | B | B | B | B | B |
| B | B | B | B | B | B | B | B | B |
| B | B | B | B | B | B | B | B | B |
| R | G | B | R | G | B | R | G | B |
| G | B | R | G | B | R | G | B | R |
| B | R | G | B | R | G | B | R | G |
| R | G | B | R | G | B | R | G | B |

TABLE 8

| R  | R | R | R  | R | R | R  | R | R |
|----|---|---|----|---|---|----|---|---|
| R  | R | R | R  | R | R | R  | R | R |
| R  | R | R | R  | R | R | R  | R | R |
| R  | R | R | R  | R | R | R  | R | R |
| GL | G | B | GL | G | B | GL | G | B |

TABLE 8-continued

| GL | G | B | GL | G | B | GL | G | B |
|----|---|---|----|---|---|----|---|---|
| GL | G | B | GL | G | B | GL | G | B |
| GL | G | B | GL | G | B | GL | G | B |

TABLE 9

| IR | IR | IR | IR | IR | IR | IR | IR | IR |
|----|----|----|----|----|----|----|----|----|
| IR | IR | IR | IR | IR | IR | IR | IR | IR |
| IR | IR | IR | IR | IR | IR | IR | IR | IR |
| IR | IR | IR | IR | IR | IR | IR | IR | IR |
| R  | G  | B  | R  | G  | B  | R  | G  | B  |
| G  | B  | R  | G  | B  | R  | G  | B  | R  |
| B  | R  | G  | B  | R  | G  | B  | R  | G  |
| R  | G  | B  | R  | G  | B  | R  | G  | B  |

TABLE 10

| UV | UV | UV | UV | UV | UV | UV | UV | UV |
|----|----|----|----|----|----|----|----|----|
| UV | UV | UV | UV | UV | UV | UV | UV | UV |
| UV | UV | UV | UV | UV | UV | UV | UV | UV |
| UV | UV | UV | UV | UV | UV | UV | UV | UV |
| R  | G  | B  | R  | G  | B  | R  | G  | B  |
| G  | B  | R  | G  | B  | R  | G  | B  | R  |
| B  | R  | G  | B  | R  | G  | B  | R  | G  |
| R  | G  | B  | R  | G  | B  | R  | G  | B  |

TABLE 11

| GL | GL | GL | GL | GL | GL | GL | GL | GL |
|----|----|----|----|----|----|----|----|----|
| GL | GL | GL | GL | GL | GL | GL | GL | GL |
| GL | GL | GL | GL | GL | GL | GL | GL | GL |
| GL | GL | GL | GL | GL | GL | GL | GL | GL |
| R  | G  | B  | IR | R  | G  | B  | IR | R  |
| G  | B  | IR | R  | G  | B  | IR | R  | G  |
| B  | R  | G  | B  | R  | G  | B  | R  | G  |
| R  | G  | B  | IR | R  | G  | B  | IR | R  |

TABLE 11

| UV | UV | UV | UV | UV | UV | UV | UV | UV |
|----|----|----|----|----|----|----|----|----|
| UV | UV | UV | UV | UV | UV | UV | UV | UV |
| UV | UV | UV | UV | UV | UV | UV | UV | UV |
| UV | UV | UV | UV | UV | UV | UV | UV | UV |
| R  | G  | B  | IR | R  | G  | B  | IR | R  |
| G  | B  | IR | R  | G  | B  | IR | R  | G  |
| B  | R  | G  | B  | R  | G  | B  | R  | G  |
| R  | G  | B  | IR | R  | G  | B  | IR | R  |

TABLE 12

| GL | GL | GL | GL | GL | GL | GL | GL | GL |
|----|----|----|----|----|----|----|----|----|
| GL | GL | GL | GL | GL | GL | GL | GL | GL |
| GL | GL | GL | GL | GL | GL | GL | GL | GL |
| GL | GL | GL | GL | GL | GL | GL | GL | GL |
| R  | G  | B  | IR | UV | R  | G  | B  | IR |
| G  | B  | IR | UV | R  | G  | B  | IR | UV |
| B  | IR | UV | R  | G  | B  | IR | UV | R  |
| IR | UV | R  | G  | B  | IR | UV | R  | G  |

Figure 8:
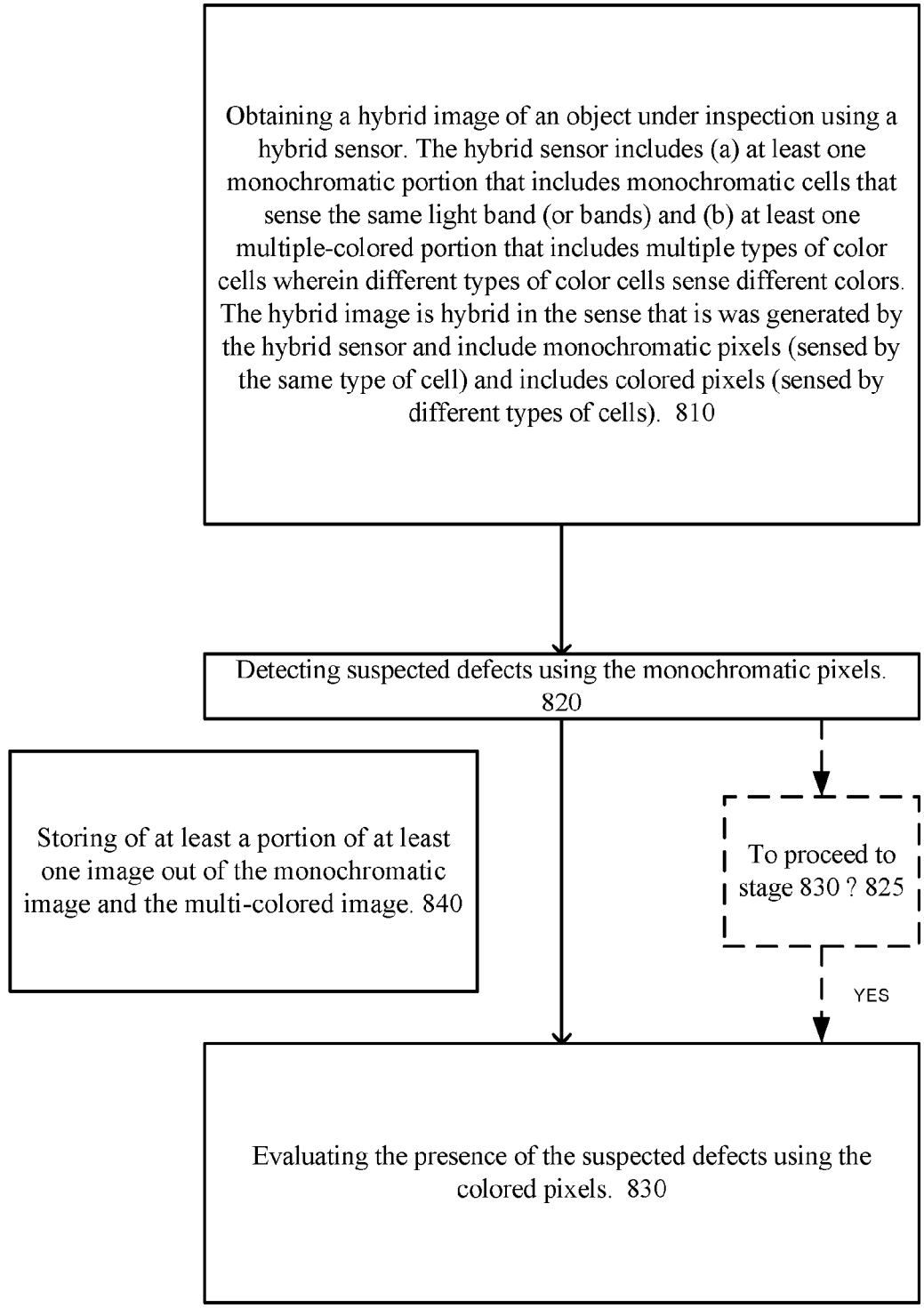
FIG. 8 illustrates a method according to an embodiment of the invention.

FIG. 8 illustrates method 800 according to an embodiment of the invention.

Method 800 may start by stage 810 of obtaining a hybrid image of an object under inspection using a hybrid sensor. The hybrid sensor includes (a) at least one monochromatic portion that includes monochromatic cells that sense the same light band (or bands) and (b) at least one multiple-colored portion that comprises multiple types of color cells wherein different types of color cells sense different colors.

The hybrid image is hybrid in the sense that is was generated by the hybrid sensor and includes monochromatic pixels (sensed by the same type of cell) and includes colored pixels (sensed by different types of cells). Thus the hybrid images can be viewed as including a monochromatic image portion and a color image portion.

Stage 810 can be executed by a hybrid sensor that has monochromatic sensing elements having a frequency band that include all the frequency bands of the color sensing elements.

Stage 810 can be executed by a hybrid sensor that has monochromatic sensing elements having a frequency band that is a broadband frequency band and the frequency bands of the color sensing elements are narrowband frequency bands.

Stage 810 can be executed by any of the hybrid sensors illustrated in this specification.

Stage 810 may be followed by stage 820 of detecting suspected defects using the monochromatic pixels.

Stage 820 may be followed by stage 830 of evaluating the presence of the suspected defects using the colored pixels.

It is noted that stage 830 can be executed whenever method 800 is executed. According to another embodiment of the invention method 800 can selectively execute stage 830— based upon the outcome of stage 820.

For example, method 800 may include stage 825 of determining whether to execute stage 830 based upon the outcome of stage 820. Stage 825 may determine to execute stage 830 of, for example, there stage 820 provides a real time indication of a defect. The relevant part of the multi-color image (corresponding to the location of the defect) can be fetched from a buffer and processed during stage 830. Stage 820 can provide an indication of the defect and the relevant portion of the multiple-color image will be stored for later processing (while other portions of the multiple-color image can be deleted or not stored for later processing).

Stage 830 can be executed in line or off line. Stage 820 can be executed by an inspection system while stage 830 can be executed by the inspection system or another system (such as a verification system). The multiple-color image can be stored and relevant portions (those who include suspected defects) can be processed by the other system.

It is noted that stage 830 may include processing only a portion of the multi-color image. The portion may be elected such as to include a suspected detect that was detected during stage 820.

Method 800 may also include stage 840 of storing of at least a portion of at least one image out of the monochromatic image and the multi-colored image. An entire image can be stored or only a portion thereof. The storage or a portion of an image can precede the processing of that image. The storing can include buffering. Short term storage (for real time image processing) and, additionally or alternatively, long term storage (for off line image processing).

Stage 820 and 830 provide a tradeoff between throughput (or simplicity of analysis) that is attributed to stage 820 and accuracy that is attributed to stage 830. Stage 830 may be viewed as providing an improved (more robust and more accurate) analysis of the suspected defects that may be used to improve the defect detection accuracy and reliability (like less false alarms) using the multi-color cells.

Stage 820 may include processing the monochromatic image to provide intermediate defect detection results.

Stage 825 may include determining whether to process the multiple-color image based upon the intermediate defect detection results.

Stage 825 may include determining to process the multiple-color image if the intermediate defect detection results are indicative of suspected defects.

Stage 825 may include determining whether to process the multiple-color image if the intermediate defect detection results are indicative of suspected defects of at least a predefined amount of probability.

Stage 810 can be executed by a hybrid sensor that provides the monochromatic image at a resolution that is higher than a resolution of the multiple-color image.

All stages of method 800 can be executed in parallel. The method can use one or more hybrid sensors as illustrated in this specification.

The invention may also be implemented in a computer program for running on a computer system, at least including code portions for performing steps of a method according to the invention when run on a programmable apparatus, such as a computer system or enabling a programmable apparatus to perform functions of a device or system according to the invention. A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc. A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with single connections that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein can be designed as either negative or positive logic signals. Therefore, in alternate embodiments, those signals described as positive logic signals may be implemented as negative logic signals, and those signals described as negative logic signals may be implemented as positive logic signals.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. An inspection system, comprising:
   a hybrid sensor that comprises:
      a monochromatic portion that is arranged to obtain a monochromatic image of a first area of an object;
      a multiple-color portion that is arranged to obtain a multi-colored image of a second area of the object;
      wherein the monochromatic portion comprises monochromatic sensing elements that sense radiation of a same frequency band;
      wherein the multiple-color portion comprises color sensing elements of different types, wherein different types of color sensing elements are associated with different frequency bands;
   a storage element arranged to store the monochromatic image and the multiple-color image; and
   a defect detection module arranged to detect defects by processing at least one of the monochromatic image and the multiple-color image.

2. The inspection system according to claim 1 wherein the defect detection module is arranged to:
   process the monochromatic image to provide intermediate defect detection results;
   determine whether to process the multiple-color image based upon the intermediate defect detection results; and
   process at least a portion of the multiple-color image to detect defects if it is determined to process the multiple-color image.

3. The inspection system according to claim 1 wherein the defect detection module is arranged to:
   process the monochromatic image to provide intermediate defect detection results;
   determine to process the multiple-color image if the intermediate defect detection results are indicative of suspected defects; and
   process at least a portion of the multiple-color image to detect defects if it is determined to process the multiple-color image.

4. The inspection system according to claim 1 wherein the defect detection module is arranged to:
   process the monochromatic image to provide intermediate defect detection results;
   determine to process the multiple-color image if the intermediate defect detection results are indicative of suspected defects of at least a predefined amount of probability; and
   process at least a portion of the multiple-color image to detect defects if it is determined to process the multiple-color image.

5. The inspection system according to claim 1, wherein the hybrid sensor is arranged to provide the monochromatic image at a resolution that is higher than a resolution of the multiple-color image.

6. The inspection system according to claim 1, wherein the frequency band of the monochromatic sensing elements comprises all the frequency bands of the color sensing elements.

7. The inspection system according to claim 1, wherein the frequency band of the monochromatic sensing elements is a broadband frequency band and wherein the frequency bands of the color sensing elements are narrowband frequency bands.

8. The inspection system according to claim 1, wherein the frequency band of the monochromatic sensing elements comprises all the frequency bands of the color sensing elements.

9. The inspection system according to claim 1, wherein the monochromatic portion comprises multiple adjacent rows of monochromatic sensing elements; and wherein the multiple-color portion comprises multiple columns, each column comprises color sensing elements that are arranged to sense a same frequency band.

10. The inspection system according to claim 1, wherein the monochromatic portion comprises multiple adjacent rows of monochromatic sensing elements; and wherein the multiple-color portion comprises multiple columns, each column comprises color sensing elements of different frequency bands.

11. The inspection system according to claim 1, wherein the monochromatic portion comprises multiple adjacent rows of monochromatic sensing elements; and wherein the multiple-color portion comprises color sensing elements of different frequency bands that are arranged in an interleaved manner.

12. The inspection system according to claim 1, wherein the hybrid sensor comprises multiple repetitions of a combination that comprises a set of monochromatic sensing elements and color sensing elements of different frequency bands.

13. The inspection system according to claim 1, wherein the hybrid sensor comprises multiple repetitions of a combination that comprises a row of monochromatic sensing elements and at least one row of color sensing elements of different frequency bands.

14. The inspection system according to claim 1, wherein the first area equals the second area.

15. The inspection system according to claim 1, wherein the first and second areas differ from each other.

16. The inspection system according to claim 1, wherein at least one frequency band comprises infra red radiation and at least one frequency band comprises visible light radiation.

17. The inspection system according to claim 1, wherein at least one frequency band comprises infra red radiation and at least one frequency band comprises ultra violet radiation.

18. The inspection system according to claim 1, wherein the monochromatic sensing elements are grouped in a group that has a shape that differs from a line.

19. A defect detection method, comprising:

obtaining a hybrid image by a hybrid sensor, the hybrid sensor comprises (a) a monochromatic portion that is arranged to obtain monochromatic image of a first area of an object; (b) a multiple-color portion that is arranged to obtain a multi-colored image of a second area of the object; wherein the monochromatic portion comprises monochromatic sensing elements that sense radiation of a same frequency band; wherein the multiple-color portion comprises color sensing elements of different types, wherein different types of color sensing elements are associated with different frequency bands; wherein the hybrid image comprises the monochromatic image and the multi-colored image; and applying a defect detection process on at least one of the monochromatic image and the multiple-color image and on at least zero reference images.

* * * * *